(12) United States Patent
Barry et al.

(10) Patent No.: US 9,278,160 B2
(45) Date of Patent: *Mar. 8, 2016

(54) INJECTABLE VOID FILLER FOR SOFT TISSUE AUGMENTATION

(71) Applicants: Baxter Healthcare S.A., Glattpark (Opfikon) (CH); Baxter International Inc., Deerfield, IL (US)

(72) Inventors: John J. Barry, Vienna (AT); Andreas Goessl, Vienna (AT); Heinz Gulle, Gross Enzersdorf (AT); Monika Mangold, Vienna (AT); Melitta Bilban, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 412 days.

This patent is subject to a terminal disclaimer.

(21) Appl. No.: 13/738,400

(22) Filed: Jan. 10, 2013

(65) Prior Publication Data

US 2013/0209370 A1 Aug. 15, 2013

Related U.S. Application Data

(63) Continuation of application No. 13/004,179, filed on Jan. 11, 2011, now Pat. No. 8,377,420, which is a continuation of application No. 12/054,990, filed on Mar. 25, 2008, now abandoned.

(60) Provisional application No. 60/920,043, filed on Mar. 26, 2007.

(51) Int. Cl.
| | | |
|---|---|---|
| *A61L 27/54* | (2006.01) | |
| *A61L 27/22* | (2006.01) | |
| *A61L 27/50* | (2006.01) | |
| *A61L 27/46* | (2006.01) | |
| *A61L 27/58* | (2006.01) | |

(52) U.S. Cl.
CPC .............. *A61L 27/54* (2013.01); *A61L 27/225* (2013.01); *A61L 27/227* (2013.01); *A61L 27/46* (2013.01); *A61L 27/502* (2013.01); *A61L 27/58* (2013.01)

(58) Field of Classification Search
None
See application file for complete search history.

(56) References Cited

U.S. PATENT DOCUMENTS

| | | | |
|---|---|---|---|
| 4,696,812 A * | 9/1987 | Silbering | ............ A61K 38/4833 128/DIG. 22 |
| 5,242,683 A | 9/1993 | Klaveness | |
| 5,752,974 A | 5/1998 | Rhee et al. | |
| 5,861,043 A | 1/1999 | Carn | |
| 6,096,309 A | 8/2000 | Prior et al. | |
| 6,287,341 B1 | 9/2001 | Lee et al. | |
| 6,605,294 B2 | 8/2003 | Sawhney | |
| 6,607,535 B1 | 8/2003 | Chan | |
| 6,703,038 B1 | 3/2004 | Schaefer et al. | |
| RE39,192 E | 7/2006 | MacPhee et al. | |
| 2001/0016646 A1* | 8/2001 | Rueger | ................... C07K 14/51 530/388.1 |
| 2003/0194389 A1 | 10/2003 | Porter | |
| 2004/0048947 A1 | 3/2004 | Lidgren et al. | |
| 2004/0068266 A1 | 4/2004 | Delmotte | |
| 2004/0101960 A1 | 5/2004 | Schaefer et al. | |
| 2005/0119746 A1 | 6/2005 | Lidgren | |
| 2005/0136038 A1 | 6/2005 | de Bruijn et al. | |
| 2006/0089715 A1 | 4/2006 | Truckai et al. | |
| 2007/0275028 A1 | 11/2007 | Barry et al. | |
| 2007/0276505 A1 | 11/2007 | Barry et al. | |
| 2008/0241072 A1 | 10/2008 | Barry et al. | |

FOREIGN PATENT DOCUMENTS

| | | |
|---|---|---|
| EP | 0 166 263 A | 1/1986 |
| WO | 95/21634 | 8/1995 |
| WO | 97/15188 | 5/1997 |
| WO | 98/57678 | 12/1998 |
| WO | 00/07639 | 2/2000 |
| WO | 03/053488 A1 | 7/2003 |
| WO | 2005/086697 | 9/2005 |
| WO | 2006/072622 A2 | 7/2006 |
| WO | 2006/072623 A1 | 7/2006 |
| WO | 2006/073711 A2 | 7/2006 |
| WO | 2007/137652 | 12/2007 |
| WO | 2008/118913 | 10/2008 |

OTHER PUBLICATIONS

Achtari, C., et al., "Les Produits Injectables et Leur Place dans le Traitement de L'Incontinence Urinaire D'Effort," *Gynakol Geburtschilfliche Rundsch*, vol. 46, 2006, pp. 39-44 (English Abstract).

Barth, A., et al., "Evaluation of Long-Term Effects of Endoscopic Injection of Collagen into the Urethral Submucosa for Treatment of Urethral Sphincter Incompetence in Female Dogs: 40 Cases (1993-2000)," *Journal of the American Veterinary Medical Association*, vol. 226, No. 1, 2005, pp. 73-76.

Brown, L. F., et al., "Fibroblast Migration in Fibrin Gel Matrices," *American Journal of Pathology*, vol. 142, No. 1, 1993, pp. 273-283.

International Preliminary Report on Patentability for for PCT/US2008/058146 mailed Oct. 29, 2009.

International Search Report and Written Opinion for PCT/US2008/058146 mailed Oct. 15, 2009.

(Continued)

*Primary Examiner* — Dennis Heyer
(74) *Attorney, Agent, or Firm* — Kilpatrick Townsend & Stockton LLP

(57) ABSTRACT

The present invention teaches a micro-porous injectable, soft elastic, fully resorbable fibrin-based composition for use as a soft tissue lumen and void filler. The composition of the present application exhibits physical characteristics, such as mechanical properties, typically seen in elastomers and mechanical stability, which is superior to fibrin alone. A variety of properties of the composition of the present invention can be effectively fine-tuned and altered by adjusting type and content of the particles as well as of the plasticizer contained in the void filler composition.

26 Claims, 3 Drawing Sheets

(56) References Cited

OTHER PUBLICATIONS

Isogai, et al., "Formation of Phalanges and Small Joints by Tissue-Engineering," *The Journal of Bone and Joint Surgery*, vol. 81-A, No. 3, Mar. 1999, pp. 306-316.

Kneser, U., et al., "Fibrin Gel-Immobilized Primary Osteoblasts in Calcium Phosphate Bone Cement: In vivo Evaluation with Regard to Application as Injectable Biological Bone Substitute," *Cells Tissues Organs*, vol. 179, 2005, pp. 158-169.

Le Guéhennec, L., et al., "A Review of Bioceramics and Fibrin Sealant," *European Cells and Materials*, vol. 8, 2004, pp. 1-11.

Parikh, S. N., "Bone Graft Substitutes: Past, Present, Future," *Journal of Postgraduate Medicine*, vol. 48, 2002, pp. 142-148.

Trout, A. T., et al., "New Fractures After Vertebroplasty: Adjacent Fractures Occur Significantly Sooner", *American Journal of Neuroradiology*, vol. 27, 2006, pp. 217-223.

Wittkampf, Albert R. M., "Augmentation of the Maxillary Alveolar Ridge with Hydroxylapatite and Fibrin Glue," *Journal of Oral and Maxillofacial Surgery*, vol. 46, 1988, pp. 1019-1021.

Wittkampf, Albert R. M., "Fibrin Glue as Cement for HA-Granules," *Journal of Cranio-Maxillofacial Surgery*, vol. 17, 1989, pp. 179-181.

Zhi, X., et al., "Management of Gastroesophageal Reflux Disease: Medications, Surgery, or Endoscopic Therapy? (Current Status and Trends)," *Journal of Long-Term Effects of Medical Implants*, vol. 15, No. 4, 2005, pp. 375-388.

\* cited by examiner

INJECTABLE VOID FILLER FOR SOFT TISSUE AUGMENTATION

CROSS-REFERENCES TO RELATED APPLICATIONS

The present application is a continuation of U.S. patent application Ser. No. 13/004,179, which was filed Jan. 11, 2011, which is a continuation of U.S. Pat No. 12/054,990, which was filed Mar. 25, 2008, which claims benefit of priority of U.S. Provisional Application No. 60/920,043, which was filed Mar. 26, 2007. The entire text of the aforementioned application is incorporated herein by reference.

FIELD OF THE INVENTION

The present invention relates generally to a micro-porous injectable, soft elastic, fully resorbable fibrin-based composition for use as a soft tissue lumen and void filler. The composition of the present application exhibits physical characteristics, such as mechanical properties, typically seen in elastomers and mechanical stability, superior to fibrin alone. According to the teachings of the present invention, a variety of properties of said void filler can be effectively fine-tuned and altered by adjusting type and content of the particles as well as of the plasticizer contained in said void filler composition.

SUMMARY OF THE INVENTION

The fibrin composition of the present invention is a natural biomaterial. It is sterilizable and has low potential toxicity. It is easy to use and the rheology permit injection and where possible minimally invasive treatment. Alteration of the fibrin modifier (plasticizer) and or particulate component can allow for fine control of water uptake, swelling, degradation and release of bioactive molecules Furthermore the invention is fully resorbable. It has negligible exotherm and exhibits elastomeric mechanical behavior making it mechanically superior to fibrin alone.

It was observed that that combining an iodinated contrast agent with calcium phosphate particles (up to 200 μm) in fibrinogen clots created a new very different material. Following this, a number of fibrin plasticizers and alternative particles were identified and the use of the composition was subsequently broadened to include other indications of hard tissue voids.

The current invention seeks to extend the possible indications for the modified fibrin composition to include soft tissue indications. These include, but are not limited to, partial or full occlusion, augmentation, or filling soft tissue lumens and voids. Lumens are taken to be the void space of tubular structures such as the vasculature, reproductive tract and gastrointestinal tract. Voids are taken to include lesions, fissures, fistulae and diverticulae. These voids can be physiological or the result of infection, surgery, cyst, tumor removal, or traumatic injury or remodeling of the soft tissue.

DETAILED DESCRIPTION OF THE INVENTION

Figure 1:
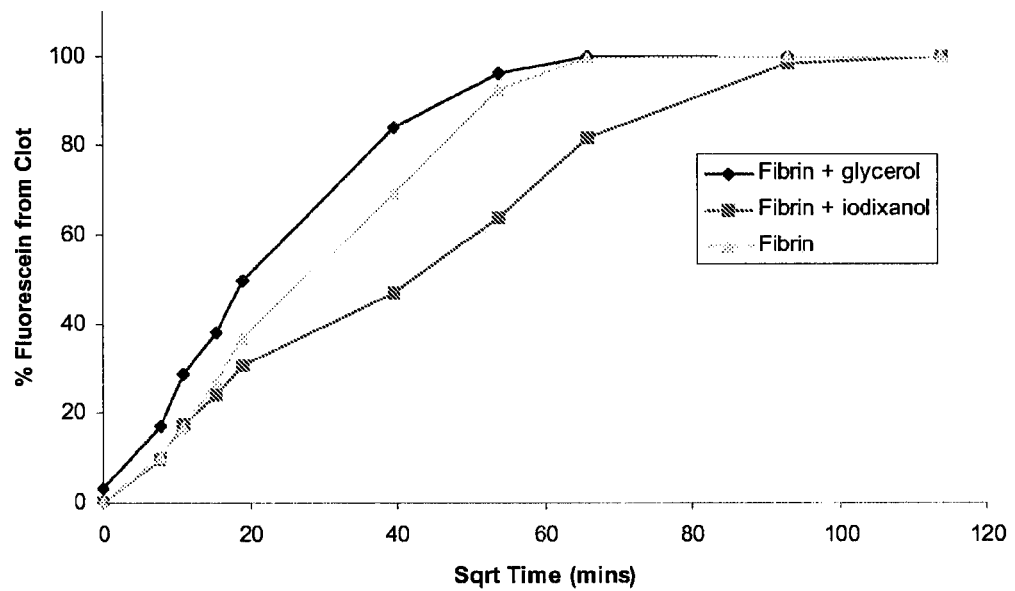
FIG. 1 shows the release of fluorescein from fibrin clots without plasticizer and with either iodixanol or glycerol.

The present invention relates generally to a multi-component system for an injectable soft tissue void filler composition, comprising:
 component (a) comprising fibrinogen;
 component (b) comprising thrombin;
 component (c) comprising at least one plasticizer; and
 component (d) comprising particles having a diameter of about 200 μm or less.

The multi-component system for an injectable soft tissue void filler composition as defined above may further include any other component suitable for augmenting, strengthening, supporting, repairing, rebuilding, healing, occluding or filling a soft tissue, such as growth factors, chemotherapeutic or pharmacological agents, biologically active agents, hardening and/or adhesive compounds and mineral additives. These compounds may be contained in any of the components (a) to (d) of the multi-component system according to the present invention or may be comprised as extra components.

According to one example of the present invention, the fibrinogen component (a) of the multi-component system as defined above may further comprise one or more of extracellular matrix proteins, for example fibronectin, cellular associated proteins, other plasma derived proteins, for example blood clotting factor XIII (FXIII) and proteases, and protease inhibitors, and mixtures thereof. The fibrinogen solution according to the present invention may also include any additive which is comprised in the state of the art for scientific and/or commercially available fibrinogen compositions, for example commercially available fibrinogen solutions.

The term "fibrinogen" includes not only fibrinogen per se, but also any clot forming substance, such as clot-forming derivatives of fibrinogen, such as "fibrin1".

The amount of fibrinogen in component (a) of the multi-component system ranges for example from about 10 to about 200 mg/ml, such as from about 30 to about 150 mg/ml or from about 75 to about 115 mg/ml.

The thrombin component (b) of the multi-component system according to the present invention, may further comprise additional compounds known in the art as well as one or both of the components (C) and (d), particularly the plasticizer component (c). There is no specific limitation in respect to the used thrombin amount. In one example of the present invention, the amount of thrombin in said thrombin component (b) is such that it is at least about 1 IU/ml in the final clotted composition such as about 30 IU/ml.

The term "thrombin" includes not only thrombin per se, but also any gelation inducing or clotting inducing agent for component (a), for example a physiologically acceptable alkaline buffer system.

The term "plasticizer", as used herein, includes any suitable substance useful in modifying the properties of the final clotted composition, for example the viscosity, the elastomeric behaviour or the mechanical stability. In one embodiment of the present invention, the plasticizer of the multi-component system as defined above has a low osmolality and allows fibrin assembly to occur at an appropriate extent.

In one example of the present invention, the suitable plasticizer of the multicomponent system according to the present invention comprises at least one biodegradable, water soluble organic compound. As used herein, the expression "biodegradable, water soluble organic compound" further includes all compounds which can be degraded in a biological environment and are at least sufficiently soluble in water, for example at temperatures in the range from about 10 to about 40° C. The term biodegradable is also taken to include plasticizers which are not degraded but are bioeliminated for example via excretory pathways.

Examples of the plasticizer of the multi-component system as defined above are selected from the group consisting of water-soluble contrast agents, polyethylene glycols, polyvalent alcohols such as glycerol (and derivates of), mono-, di-, tri- and polysaccharides and any combination thereof.

In one example of the present invention, the suitable contrast agent of the multi-component system according to the present invention comprises at least one iodine containing organic compound. In a further example of the present invention, organic compounds containing rare earth elements such as gadolinium can be used.

As used herein, the term "iodine containing organic compound" includes all compounds which contain at least one iodine atom and/or iodine ion, bonded either physically or chemically, for example covalently or co-ordinatively. The same definition applies mutatis mutandis to the above-mentioned organic compound containing rare earth elements.

Examples of contrast agents, without being limited thereto, are diatrizoate (meglumine), iodecol, iodixanol, iofratol, iogulamide, iohexol, iomeprol, iopamidol, iopromide, iotrol, ioversol, ioxaglate and metrizamide and mixtures thereof.

According to one example of the present invention, the amount of plasticizer in component (C) is such that it ranges from about 10 to about 80% w/v, such as from about 15 to about 60% w/v or from about 20 to about 40% w/v, in the final clotted composition.

The term "particle" includes any type of particle shape or form known in the art, for example spherical, angular or hollow.

In one embodiment of the present invention, the particles of the multi component system according to the present invention are biodegradable and/or biocompatible, non-toxic, non-watersoluble, inorganic and/or organic. The particles comprise, for example, substances selected from the group consisting of calcium salts such as tricalcium phosphate, alpha-tricalcium phosphate, beta-tricalcium phosphate, calcium phosphate, a polymorph of calcium phosphate, hydroxyapatite, calcium carbonate, calcium sulfate, polymeric compounds such as polyactide, polyglycolide, polycaprolactone, polytrimethylene carbonate, polyethylene glycol and random or ordered copolymers thereof, biodegradable or biocompatible glasses and ceramics and any combination thereof. In one example, the particles are selected from the group consisting of tricalcium phosphate, alpha-tricalcium phosphate, betatricalcium phosphate and calcium phosphate and mixtures thereof, having a Ca/P ratio in the range of about 1.5 to about 2. The particles of the present invention further include all commercially available compounds and/or mixtures known in the art to be used within the meaning of component (d). According to another example, said particles of the multi-component system of the present invention have a diameter of less than about 100 μm, for example less than about 50 μm. In one specific example of the present invention the amount of the particles in component (d) ranges from about 1 to about 50% w/w, such as from about 10 to about 45% w/w or from about 30 to about 40% w/w in respect to the final clotted composition.

According to one embodiment of the present invention, the amount of fibrinogen in component (a) of the multi-component system as defined above ranges from about 10 to about 200 mg/ml, the amount of thrombin in component (b) is such that it is at least about 1 IU/ml in the final clotted composition, the amount of plasticizer contained in component (c) is such that it ranges from about 10 to about 80% w/v in the final clotted composition, and the amount of the particles in component (d) ranges from about 1 to about 50% w/w in respect to the final clotted composition.

According to a specific example of the present invention, the amount of fibrinogen in component (a) of the multi-component system as defined above ranges from about 75 to about 115 mg/ml, the amount of thrombin in component (b) is such that it ranges from about 25 IU/ml to about 50 IU/ml in the final clotted composition, the amount of plasticizer contained in component (C) is such that it ranges from about 30 to about 50% w/v in the final clotted composition, and the amount of the particles in component (d) ranges from about 30 to about 40% w/w in respect to the final clotted composition.

In another embodiment of the present invention, the multi-component System for an injectable void filler composition, comprises:
  component (a) comprising fibrinogen;
  component (b) comprising thrombin;
  component (C) comprising at least one plasticizer; and
  component (d) comprising particles having a diameter of about 200 μm or less; wherein one or more or all of the components (a) to (d) are present in a solid form.

The multi-component system according to the present invention may contain the components either in form of a solution or of a dispersion or of a solid, for example as a lyophilisate, or any combination thereof. Further, the components in said multi-component system may be present in containers suitable for storage, transportation or use of said multi-component system. The containers usable in the multi-component system according to the present invention are not limited in any way but include containers of any size, material or shape, for example vials or syringes.

Moreover, the components of said multi-component system may for example be contained in different containers or may be present in the same container in any combination, for example as a combination of components (b) and (c) in one container and of components (a) and (d) each in different containers.

According to the present invention, the containers may for example contain one or more components as a solid, as well as a solvent separated from said components by a separation means in said container, wherein a solution of the respective one or more components can be prepared by breaking or removing said separation means. The components (a) to (d) of the multi-component system of the present invention may be also present as a ready-to-use mixture.

Moreover, said components (a) to (d) present in one or more containers may also be part of a kit, comprising the multi-component system as defined above. The kit may further comprise any additional compound usable in the multi-component system of the present invention, for example auxiliary agents, buffer salts or buffer solutions. The kit as defined above may also contain means for mixing the components, for example syringes, Luer adapters, tubes, extra containers, etc.

Another aspect of the present invention relates to an injectable void filler composition, comprising:
  component (a) comprising fibrin;
  component (b) comprising thrombin;
  component (c) comprising at least one plasticizer; and
  component (d) comprising particles having a diameter of about 200 μm or less.

According to one example of the present invention, the injectable soft tissue void filler composition is prepared from the multi-component system as defined above, for example by mixing the components of said multi-component system together and/or homogenizing said components. The preparation of the injectable soft tissue void filler composition can be carried out at any suitable temperature, such as in the range from about 18 to about 37° C., for example at 25° C.

Moreover, the injectable soft tissue void filler composition as defined above may further include any other component suitable for e.g. augmenting, strengthening, supporting, repairing, rebuilding, healing, occluding or filling a void, such as growth factors, chemotherapeutic or pharmacological agents, biologically active agents, hardening and/or adhesive compounds and mineral additives. These compounds and/or agents can be chemically attached to the matrix, adsorbed on the particulate component, for example on calcium salt containing particles, trapped in the fibrin matrix or contained as a free molecule/drug particle, for example a powder.

The components (b) to (d) of the injectable soft tissue void filler composition according to the present invention are the same as defined for the multi-component system characterized above.

The term "fibrin" does not only refer to fully coagulated fibrinogen but further includes any mixture of fibrin and fibrinogen which may occur during formation of fibrin from fibrinogen using thrombin and, thus, includes any ratio of fibrinogen/fibrin and any grade of gelation and/or clotting conceivable as long as it has no negative impact on the final composition injected into the void. The fibrin component (a) of the injectable void filler composition of the present invention further includes fibrin with only a small amount of fibrinogen or without any fibrinogen left in said fibrin. Moreover, the term "fibrin" further includes any partly or fully gelled or clotted form of component (a) as defined above.

According to one example of the present invention, the amount of fibrin in said fibrin component (a) of the injectable void filler composition as defined above ranges from about 5 to about 100 mg/ml, such as from about 15 to 65 mg/ml or from about 30 to 65 mg/ml in the final clotted composition.

According to another example, the amount of fibrin in said fibrin component (a) of the injectable void filler composition of the present invention ranges from about 5 to about 100 mg/ml in the final clotted composition, the amount of thrombin in component (b) is at least about 1 IU/ml in the final clotted composition, the amount of plasticizer contained in component (c) ranges from about 10 to about 80% w/v in the final clotted composition, and the amount of particles in component (d) ranges from about 1 to about 50% w/w in respect to the final clotted composition.

According to the present invention, the injectable void filler composition as defined above is in a gelled or clotted state and has a viscosity suitable for injecting into soft tissue void.

As used herein, the term "gelled" means any state of elevated viscosity when compared to the initial state. This can be observed for example in the formation of fibrin from fibrinogen or in a finely dispersed system of at least one solid phase and at least one liquid phase, such as a colloid. Further, the term "gelled" includes all states of gelation known in the art.

The term "clotted" means, for example, a gel comprising fibrin and includes any kind of coagulation state known in the art.

The examples presented below are provided as a guide to how the material could be utilized to occlude, augment or fill soft tissue lumen and voids and are not to be construed as limiting the invention in any way.

| Materials: | |
|---|---|
| Fibrin sealant solution | Freeze dried fibrinogen powder reconstituted with, aprotinin solution to a total clottable protein concentration of 91 mg/ml. |
| Iodixanol | 5-[acetyl-[3-[acetyl-[3,5-bis(2,3-dihydroxy-propylcarbamoyl)-2,4,6-triiodo-phenyl]-amino]-2-hydroxy-propyl]-amino]-N,N'-bis(2,3-dihydroxypropyl)-2,4,6-triiodo-benzene-1,3-dicarboxamide |
| Iohexol | 5-(acetyl-(2,3-dihydroxl-propyl)-amino)-N,N'-bis(2,3-dihydroxypropyl)-2,4,6-triiodo-benzene-1,3-dicarboxamide |
| Fluorescein | 2-(6-hydroxy-3-oxo-xanthen-9-yl)benzoic acid |
| Particles | Tricalcium phosphate particles (TCP), 35 µm, spherical (Plasma Biotal, Derby UK) Hydroxyapatite (HA) particles derived from ground MBCP 60% HA/40% TCP, Biomatlante, France. |
| Phosphate Buffer Solution | Phosphate Buffered NaCl (0.85% saline) buffered to pH 7.2 |
| Thrombin | 500 IU/ml Freeze dried thrombin powder reconstituted with 5 ml of thrombin buffer, to a concentration of 500 IU/ml. |
| Thrombin Buffer | 40 mM $CaCl_2$ in $H_2O$ |

EXAMPLE 1

Preparation of Void Filler Composition (Containing Fibrin, Plasticizer and a Candidate Drug) for the Treatment of Fistulae In this example the composition is intended for injection into soft tissue voids where filling and local drug delivery is a requirement. An example of such a requisite would be in the treatment of fistulae where the void could be filled with an antibiotic releasing material. The fibrin functions as a biological matrix allowing fibroblast attachment/infiltration and natural healing to occur (Brown et al 1993). Furthermore the use of a contrast agent as the plasticizer allows visualization and control of the application.

In this example the term antibiotic is meant to describe any antimicrobial agent that can produce a desired therapeutic effect. It includes the "classical" antibiotics from the groups aminoglycosides/carbacephems/carbapenems/cephalosporins/glycopeptides/mar-olides/monobactams/penicillins/polypeptides/sulfonamides and tetracylides (soluble in water or organic solvents) and newly identified antimicrobial agents such as particulate/colloidal silver or bismuth thiols.

The term fistulae in this context is taken to mean non-branched simple fistulae from the groups (but not limited to) anal fistulae, ano-rectal fistulae, arteriovenous fistulae, gastric fistulae, intestinal fistulae vaginal fistulae and broncho-oesophageal fistulae. The "liquidity" of the composition for a period of time post-mixing may allow for better filling of more complex fistulae and increased success rates when treating them (when compared to normal fibrin). However further investigation is required to demonstrate this.

Method:

The composition is injected as a liquid into a void (mould). After 1 hr the clotted compositions are transferred to a phosphate buffer saline solution and the fluorescein release measured.

Clots with glycerol: A 40% plasticizer (glycerol) and 10 IU/ml thrombin solution is prepared in a thrombin dilution buffer (40 mM $CaCl_2$ in double distilled water). The solution is then homogenized. The solution is centrifuged to remove bubbles and sterilized by filtering through a 0.22 μm filter. The fibrinogen is mixed with thrombin/plasticizer in a 1:1 ratio (therefore the plasticizer concentration in the gelled clot is halved).

For this 1 ml of the glycerol/thrombin solution is transferred to a 5 ml syringe. 1 ml of fibrinogen (91 mg/ml) is transferred to a separate 5 ml syringe. The particles (dry powdered fluorescein 0.05 g) are weighed and placed into another 5 ml syringe.

The syringes containing the particles and the thrombin are connected via a Luer adapter and the thrombin/glycerol and particles homogenized by transferring the contents from syringe to syringe thoroughly.

The syringes containing the thrombin/glycerol/particles and the fibrinogen are connected via a Luer adapter and the contents homogenized.

The material remains liquid for approximately 1-1.5 minutes. During this time it can be injected into the defect or alternatively after a few minutes it can be delivered as a preformed gel.

Clots with iodixanol: A 60% plasticizer (iodixanol) and 75 IU/ml thrombin solution is prepared in a thrombin dilution buffer (40 mM $CaCl_2$ in double distilled water). The solution is then homogenized. The solution is centrifuged to remove bubbles and sterilized by filtering through a 0.22 μm filter. The fibrinogen is mixed with thrombin/plasticizer in a 1:1 ratio (therefore the plasticizer concentration in the gelled clot is halved to 30%).

For this 2 ml of the thrombin/contrast agent solution is transferred to a 5 ml syringe. 1 ml of fibrinogen (91 mg/ml) is transferred to a separate 5 ml syringe. The particles (dry powdered fluorescein 0.05 g) are weighed and placed into another 5 ml syringe.

The syringes containing the particles and the thrombin are connected via a Luer adapter and the thrombin/CA and particles homogenized by transferring the contents from syringe to syringe thoroughly.

The syringes containing the thrombin/CA/particles and the fibrinogen are connected via a Luer adapter and the contents homogenized. The material remains liquid for approximately 1 minute during this time it can be injected into the void or alternatively after a few minutes it can be delivered as a preformed gel.

The release of fluorescein from fibrin clots without plasticizer and with either iodixanol or glycerol can be taken from FIG. 1. The presence of the plasticizer in addition to changing the material properties alters the release of the candidate drug allowing a faster or a more prolonged/sustained release thereby allowing tailoring of the antimicrobial activity.

EXAMPLE II

Composition Containing Fibrin, a Contrast Agent and Calcium Phosphate for Use as a Bulking Agent in the Treatment of Urinary Stress Incontinence In 1994, collagen injection to augment the urethral sphincter received FDA approval for the treatment of stress incontinence associated with intrinsic sphincter deficiency (ISD) in women, and post-prostatectomy incontinence in men. Bovine collagen still remains the gold standard despite problems such as allergic reaction and failure due to biodegradation (Achtari et al, 2006). Although The literature does suggest that the failure of the collagen is linked more to a flattening of the collagen deposits rather than the resorption of the collagen (Barth et al, 2005). While many of the new bulking agents that are being investigated are seeking to use non-degradable materials they are also trying to use materials that have viscosities and elasticities closer to that of the natural tissue.

The fibrin/contrast agent/hydroxyapatite composition in this example can be used in place of collagen. The composition is a soft elastic material better suited to the application than fibrin alone which would collapse in a similar fashion to collagen.

The fibrin/contrast agent/hydroxyapatite composition as defined above may also include any other component suitable for promoting natural tissue repair. An example of such a molecule would be BMP-2. A more extensive list of preferred growth factors/bioactive agents is detailed in the assigned U.S. Pat. No. 5,752,974, which is hereby incorporated by reference. These compounds and/or agents can be chemically attached to the matrix, adsorbed on the particulate component, for example on calcium salt containing particles, trapped in the fibrin matrix or contained as a free molecule/drug particle, for example a powder.

Method:

Either an 80% or a 60% plasticizer (contrast agents iodixanol or iohexol) and a 75 IU/ml thrombin solution is prepared in a thrombin dilution buffer (40 mM $CaCl_2$ in double distilled water). The solution is then homogenised. The solution is centrifuged to remove bubbles and sterilized by filtering through a 0.22 μm filter. The fibrinogen is mixed with thrombin/contrast agent (CA) in a 1:1 ratio (therefore the plasticizer concentration in the gelled clot is halved to either 40 or 30%).

For this 2 ml of the thrombin/contrast agent solution is transferred to a 5 ml syringe. 2 ml of fibrinogen (91 mg/ml) is transferred to a separate 5 ml syringe. The calcium phosphate particles (ca. 35 μm) are incorporated as percentage weight of the final clot volume (w/v). These are weighed and placed into another 5 ml syringe.

The syringes containing the particles and the thrombin are connected via a Luer adapter and the thrombin/CA and particles homogenised by transferring the contents from syringe to syringe thoroughly. The syringes containing the thrombin/CA/particles and the fibrinogen are connected via a Luer adapter and the contents homogenised. The material remains liquid for approximately 1 minute during this time it can be injected into the defect or alternatively after a few minutes it can be delivered as a pre-formed gel.

Figure 2:
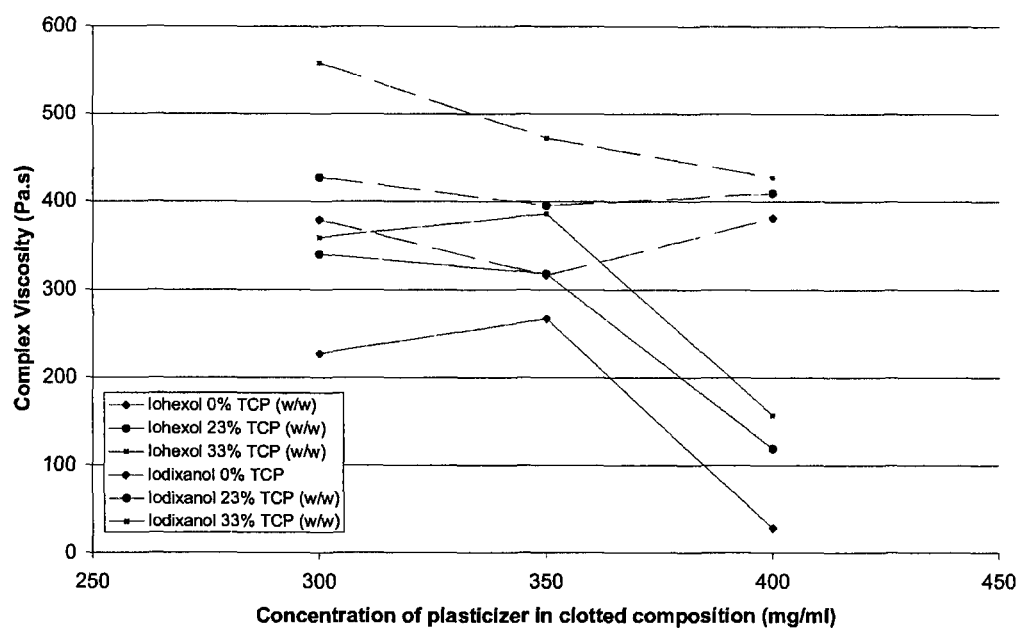
FIG. 2 shows the elasticity of the material and the varying the viscosity of the clots with different concentrations of contrast agents; and, FIG. 3 shows rheological data of compositions containing iodixanol as a plasticizer and increasing amounts of calcium salts.
Figure 3:
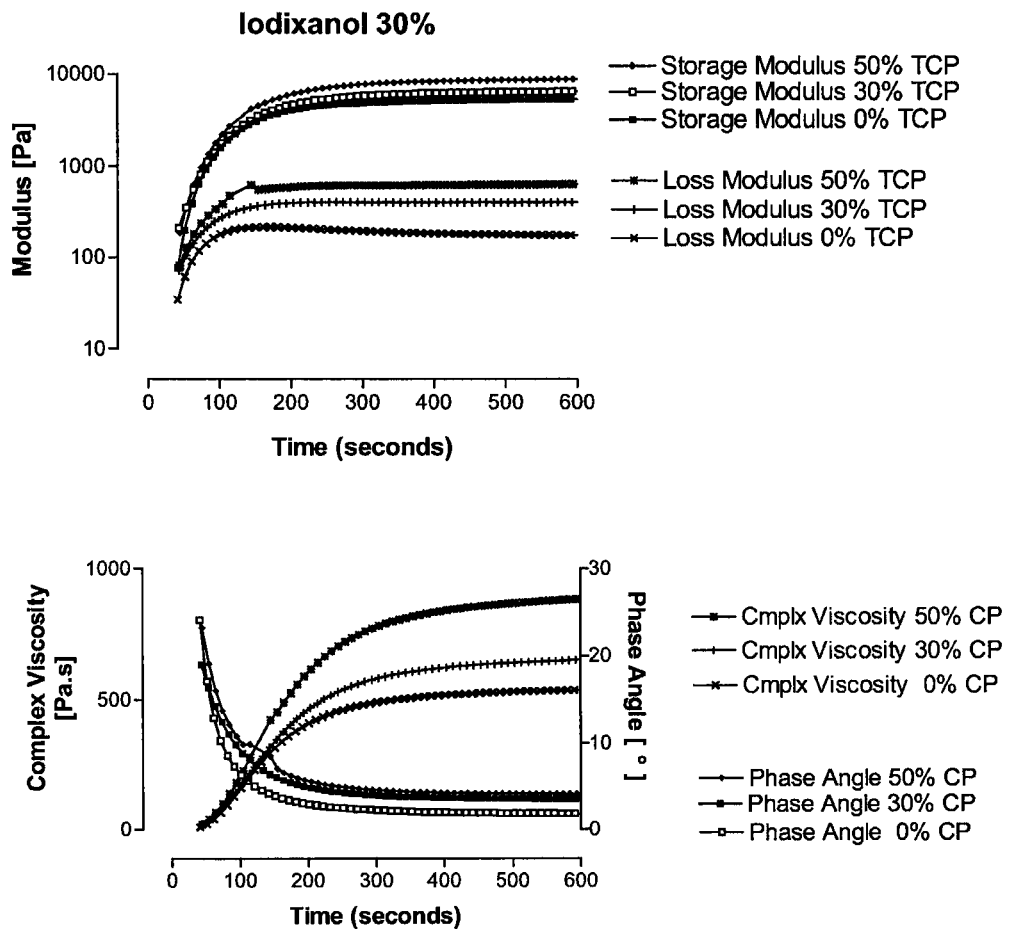

The attached figures demonstrate why the invention composition represents a good alternative to collagen. The elasticity of the material and the ability to tailor the viscosity of the respective clots with different concentrations of contrast agents and of TCP can be taken from FIG. 2. Rheological data of compositions containing iodixanol as plasticizer and increasing amounts of calcium salts can be taken from FIG. 3.

The composition can also be considered for use as a bulking agent for the cardiac sphincter in the treatment of Gastroesophageal Reflux Disease (GERD). While the treatment of GERD by this method has been found to be both feasible and safe (Zhi et al, 2005), it is possible that the presence of the x-ray opacifier can allow real time monitoring of the procedure and prevent injection transmurally through the wall of the esophagus. Complications such as this can be undetected at the time of the procedure and can lead to adverse effects.

EXAMPLE III

Tissue Occlusion

Occlusive devices are usually swellable materials. Some plasticizers confer this property on the invention composition. This is mainly due to the to the large plasticizer molecule being trapped in the composition and is unable to diffuse rapidly from the matrix. The net result is water uptake and swelling of the material to balance the osmotic forces.

Bone Plugs: are well know in the art (U.S. Pat. No. 6,607, 535, U.S. Pat. No. 5,861,043 which are herein incorporated by reference) and are used to restrict or prevent passage of bone cement into the medullary canal during hip replacement surgery. In U.S. Pat. No. 6,605,294, a rapidly hydrating hydrogel plug to occlude the femoral canal is introduced. These hydrogel bone plugs are non-weight bearing but are expected to have significant benefits over non-degradable polyethylene plugs which remain as part of the implant. An injectable fibrin composition containing iodixanol and tricalcium phosphate could also be used as a bone plug. The composition in Example 2 is a rapidly hydrating matrix which swells on contact with fluid ensuring a tight fit between the invention composition and the femoral canal. Further advantages of using the invention composition is that it can be delivered minimally invasively and the delivery can be monitored due to the presence of the x-ray opacifier.

Reversible Sterilization The injectable fibrin composition can be delivered via catheter for the prevention of pregnancy as described in the assigned U.S. Pat. No. 5,752,974. By this method the composition is injected such that the Fallopian tubes are filled/blocked. The rapid hydration and swelling of the composition prevents the egg and or sperm from passing through or around the composition. The fibrin would then function as a biological matrix allowing natural healing and fibrous scar tissue formation to occur (Brown et al 1993). Bioactive molecules (such as epidermal growth factor (EGF), transforming growth factor-alpha (TGF-[alpha]), transforming growth factor-beta (TGF-[beta]), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), and/or platelet derived growth factor (PDGF)) can also be incorporated in the matrix to further support/promote tissue formation. A complete set of therapeutic agents that could be delivered in this fashion are listed in assigned Patent WO 2005086697 and is hereby incorporated by reference. The procedure can be reversed by excision of the blocked portion and reconnection of the tube.

Dental Occlusion The invention composition would be used to occlude and seal the gum line following dental surgery. The composition is allowed to hydrate, swell and occlude providing a barrier against oral fluids/food materials and bacteria. The absorbable composition will be degraded and replaced by natural tissue.

Vascular Occlusion: can be used to limit or block blood flow in a blood vessel during a surgical technique or during the treatment of a pathophysiology. Examples of such pathophysiologies could be the limiting the blood flow to a tumor or an aneurysm. The ability to deliver therapeutics agents along with the composition may further increase the suitability of the composition. In the case of an aneurysm the blood flow to the weakened vessel could be restricted and a vasoactive molecule incorporated to allow remodeling of the vasculature around the weakened vessel. The advantage of the invention composition is the swelling to ensure a good fit between the composition and the vessel. Alteration of the fibrin plasticizer can allow for fine control of water uptake, swelling, degradation and release of the therapeutic agents.

EXAMPLE IV

Local Drug Delivery

The use of the composition as a local drug delivery vehicle to treat diseased states such as cardiovascular disease, degenerative disc disease, bleeding peptic ulcers or the treatment of tumors. The composition can be injected as a liquid, or a pre-formed gel, into/adjacent to or distant to the affected tissue. The site specific delivery of the material would avoid the necessity of a high systemic dose to achieve efficacious dose levels in the tissue. Thus reducing the likelihood of toxicity. It is also possible that the composition can functional mechanically in addition to releasing a therapeutic. For example in a bleeding peptic ulcer, the invention composition can be injected adjacent to the ulcer where it would act mechanically to restrict blood flow to the area. This effect would be enhanced by the local delivery of the vasoconstrictor epinephrine. Similarly the use of the formulation could be used to provide mechanical support in degenerative disc repair while simultaneously delivering anti-inflammatory or steroidal agents.

Cytotoxins and/or antibodies, analgesics, anticoagulants, anti-inflammatory compounds, antimicrobial compositions, cytokines, drugs, growth factors, interferons, hormones, lipids, deminearlized bone or bone morphogenetic proteins, cartilage inducing factors, oligonucleotides, polymers, polysaccharides, polypeptides, protease inhibitors, vasoconstrictors vasodilators, vitamins and minerals (Pat. RE39192), the enhanced material properties of the current invention and the ability to tailor the release rates (FIG. 1.) make this more suitable as a local drug delivery vehicle. Suitable classes of therapeutics include but are not limited to vasoactive agents, neuroactive agents, hormones, growth factors, cytokines, anesthetics and muscle relaxants, steroids, antibiotics, anticoagulants, anti-inflammatory agents, anti-proliferating agents, antiulcer agents, antivirals, immuno-modulating agents, cytotoxic agents, prophylactic agents, antigens and antibodies. A complete set of therapeutic agents that could be delivered in this fashion are listed in the assigned patents WO 2005086697 and U.S. Pat. No. 6,605,294 which are hereby incorporated by reference in their entireties.

What is claimed is:

1. A method of treating a soft tissue lumen of a patient, wherein the soft tissue lumen is located in the vasculature, reproductive tract, or gastrointestinal tract of the patient, the method comprising:
    preparing a composition by combining a fibrinogen component, a thrombin component, a plasticizer, and calcium-containing particles having an average diameter between 0.01 µm and 200 µm; and
    delivering the composition to the soft tissue lumen of the patient.

2. The method according to claim 1, wherein the plasticizer is a member selected from the group consisting of a contrast agent, a polyethylene glycol, a polyvalent alcohol, a monosaccharide, and a saccharide polymer.

3. The method according to claim 1, wherein the plasticizer is a contrast agent.

4. The method according to claim 3, wherein the contrast agent is selected from the group consisting of gadolinium, diatrizoate, iodecol, iodixanol, iofratol, iogulamide, iohexol, iomeprol, iopamidol, iopromide, iotrol, ioversol, ioxagulate, and metrizamide.

5. The method according to claim 4, wherein the contrast agent is iodixanol.

6. The method according to claim 4, wherein the contrast agent is iohexol.

7. The method according to claim 1, wherein the plasticizer is glycerol.

8. The method according to claim 1, wherein the plasticizer is a biodegradable, water soluble organic compound.

9. The method according to claim 1, wherein calcium-containing particles are present at between 1% and 50% w/w of the composition.

10. The method according to claim 1, wherein the composition is delivered to the soft tissue lumen as a liquid.

11. The method according to claim 1, wherein the composition is delivered to the soft tissue lumen as a gel.

12. A method of treating a soft tissue void of a patient, wherein the soft tissue void is a fistula or a diverticulum of the patient, the method comprising:
   preparing a composition by combining a fibrinogen component, a thrombin component, a plasticizer, and calcium-containing particles having an average diameter between 0.01 µm and 200 µm; and
   delivering the composition to the soft tissue void of the patient.

13. The method according to claim 12, wherein the plasticizer is a member selected from the group consisting of a contrast agent, a polyethylene glycol, a polyvalent alcohol, a monosaccharide, and a saccharide polymer.

14. The method according to claim 12, wherein the plasticizer is a contrast agent selected from the group consisting of gadolinium, diatrizoate, iodecol, iodixanol, iofratol, iogulamide, iohexol, iomeprol, iopamidol, iopromide, iotrol, ioversol, ioxagulate, and metrizamide.

15. The method according to claim 12, wherein the plasticizer is iodixanol.

16. The method according to claim 12, wherein the plasticizer is iohexol.

17. The method according to claim 12, wherein the plasticizer is glycerol.

18. The method according to claim 12, wherein the composition is delivered to the soft tissue lumen as a liquid.

19. The method according to claim 12, wherein the composition is delivered to the soft tissue lumen as a gel.

20. A method of treating a soft tissue lumen of a patient, wherein the soft tissue lumen is a void space of a tubular structure of the patient, the method comprising:
   preparing a composition by combining a fibrinogen component, a thrombin component, a plasticizer, and calcium-containing particles having an average diameter between 0.01 µm and 200 µm; and
   delivering the composition to the soft tissue lumen of the patient.

21. The method according to claim 20, wherein the plasticizer is a member selected from the group consisting of a contrast agent, a polyethylene glycol, a polyvalent alcohol, a monosaccharide, and a saccharide polymer.

22. The method according to claim 20, wherein the plasticizer is iodixanol.

23. The method according to claim 20, wherein the plasticizer is iohexol.

24. The method according to claim 20, wherein the plasticizer is glycerol.

25. The method according to claim 20, wherein the composition is delivered to the soft tissue lumen as a liquid.

26. The method according to claim 20, wherein the composition is delivered to the soft tissue lumen as a gel.

* * * * *